United States Patent [19]

Pulsmeier et al.

[11] Patent Number: 4,536,971
[45] Date of Patent: Aug. 27, 1985

[54] APPARATUS FOR TESTING THE AIR-PERMEABILITY OF LENGTHS OF TEXTILES

[76] Inventors: Harald Pulsmeier, Hamischerstr., D-5163 Langerwehe-Heistern; Walter Best, Merowingerstr. 8, D-5160 Dueren, both of Fed. Rep. of Germany

[21] Appl. No.: 582,719

[22] Filed: Feb. 23, 1984

[30] Foreign Application Priority Data

Feb. 25, 1983 [DE] Fed. Rep. of Germany ... 8305292[U]

[51] Int. Cl.³ ............................................. F26B 9/06
[52] U.S. Cl. .......................................... 34/89; 73/38; 73/159
[58] Field of Search ................ 73/38, 159; 34/89, 155

[56] References Cited

U.S. PATENT DOCUMENTS

| | | | |
|---|---|---|---|
| 2,350,058 | 5/1944 | May | 73/38 |
| 2,755,660 | 7/1956 | Kammermeyer et al. | 73/38 |
| 3,577,767 | 5/1971 | Stedile | 73/38 |
| 4,191,046 | 3/1980 | Baker et al. | 73/38 |
| 4,401,147 | 8/1983 | Beck et al. | 73/38 |

*Primary Examiner*—Larry I. Schwartz
*Attorney, Agent, or Firm*—Shlesinger, Arkwright, Garvey & Fado

[57] ABSTRACT

An air-permeability measuring apparatus for textiles includes a measuring fork having first and second rigid legs disposed in parallel overlying relations. A first double pipe stub is displacably mounted to the first leg and has inner and outer stub parts providing an inner flow channel and an annular flow channel. A second double pipe stub is mounted into the second leg and includes inner and outer stub parts providing a second inner flow channel and a second annular flow channel. The double pipe stubs are coaxial and the first double pipe stub is adapted for being displaced between an insert position and a clamping position and in the clamping position the inner and annular flow channels are aligned and communicate. A pipe extends from each of the second inner and annular flow channels and the pipes are connected to an exhauster which exerts a vacuum on the inner and annular flow channels and thereby induces air flow therethrough. A control valve is disposed in the pipe extending from the second annular flow channel and regulates the air flow therewith. A measuring apparatus is associated with the pipe extending from the inner flow channel and measures the air flow therethrough. A control system is operably connected to the control valve and the exhauster and assures constant pressure on each of the inner and annular flow channels.

40 Claims, 4 Drawing Figures

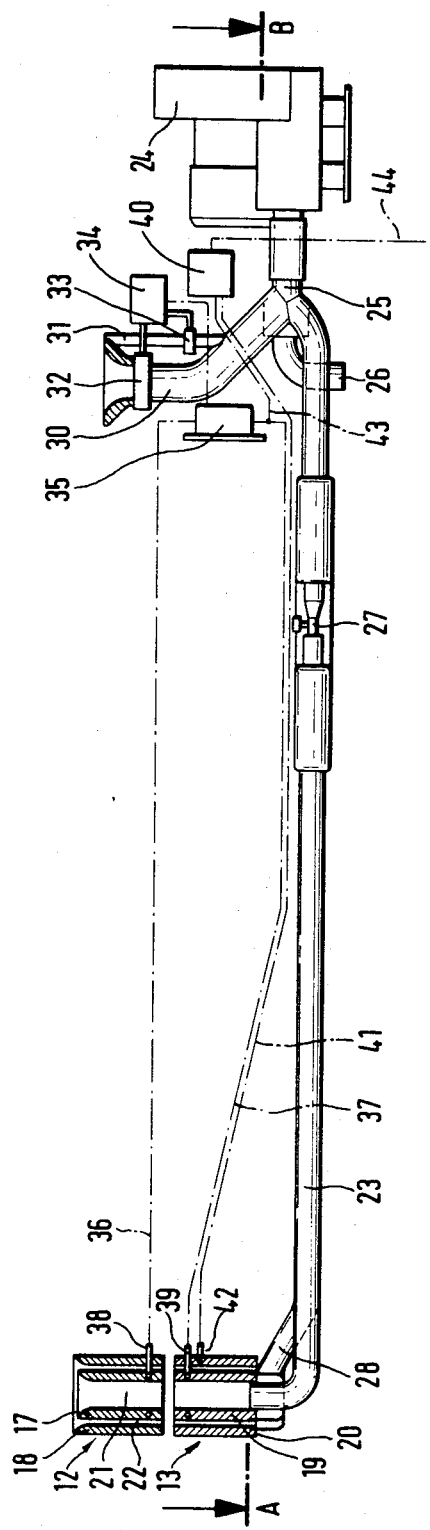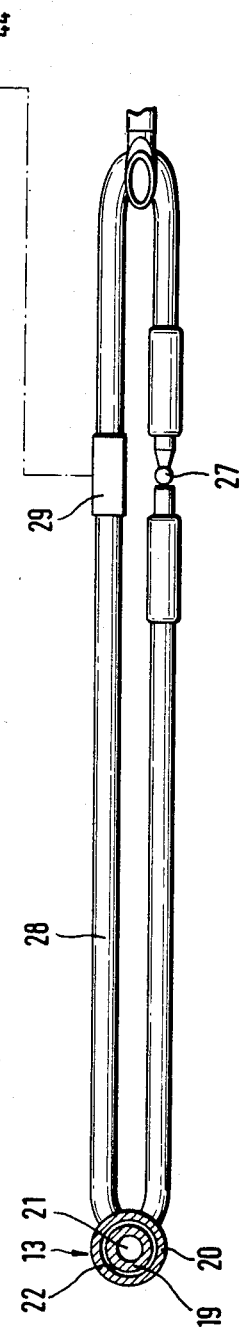

APPARATUS FOR TESTING THE AIR-PERMEABILITY OF LENGTHS OF TEXTILES

BACKGROUND OF THE INVENTION

The invention concerns an apparatus for testing the air-permeability of lengths of textiles, in particular of substantially incompressible paper-machine felts or dryer fabrics, and includes a testing fork with rigid, mutually spaced and essentialy mutually parallel legs to the free ends of each of which mounted one pipe stub, at least one of said stubs being displaceable by means of a clamping device for clamping a length of fabric between the pipe stubs. The displaceable pipe stub is movable with respect to the associated leg in essentially coaxial manner and toward the other pipe stub. The other pipe stub is connected by an air pipe disposed largely in rectilinear manner, in the relevant leg to a motor-driven exhauster, both the motor and the exhauster being mounted in a frame joining the two legs. At least one control means for setting the flow rate, at least one vacuum gauge, preferably a first differential-pressure meter, and at least one air volumeter or air-flow-rate meter being further provided in the air pipe for controlling and regulating the device.

Such a test apparatus is described in the German Gebrauchsmuster No. 82 16 624. It has proven itself by providing accurate and, most importantly, reproducible test values. However, spurious test results are frequently incurred when the air-permeability of a largely incompressible length of material, for instance a spiral fabric or a dryer fabric made of monofilamentary, synthetic or multilayer woven yarns, or dryer fabrics containing glass fibers, is measured. This is due to the edge seals being inadequate, and therefore spurious air can enter laterally into the pipe stubs which are connected to the air pipe.

It is therefore the object of the invention to so further develop the known testing apparatus that the entry of spurious air is prevented when measuring largely incompressible lengths of materials.

This problem is solved by the invention in that at least the pipe stub which is connected to the air pipe is designed as a double pipe stub having mutually coaxial inner and outer pipe parts. The air pipe is connected to the inner pipe part of the relevant double pipe stub and the outer pipe part is connected to a parallel pipe entering the air pipe and passing within the relevant leg between the air volumeter or airflow rate meter and the exhauster. A control valve to set the degree of vacuum is mounted in said parallel pipe, and the outer pipe part and the inner pipe part of the immobile double pipe stub are connected to a second differential-pressure meter.

This second differential-pressure meter regulates the control valve in the parallel pipe so that the pressures inside the inner pipe part and in the annular space between the inner and outer pipe parts are equal, that is, there is no pressure difference. Consequently no spurious air can enter the inner pipe part and thereby float to the volumeter or airflow rate meters, which would introduce a spurious component in the measurements. Thus, what is measured is the actual air moving through the cross-section of the inner pipe part and passing through the length of material.

Preferably, both pipe stubs are designed as double pipe stubs, the mutually opposite edges of the inner and outer pipe parts always being congruent. The clear spacing betwen the inner and outer pipe parts always being be at least 5 mm.

Appropriately, the inner and outer pipe parts are mutually joined in rigid manner by means of brackets and the like.

It is particularly advantageous to connect the control valve in the parallel pipe with a control motor which in turn is connected to a vacuum regulator connected to the second differential-pressure meter. Any pressure difference that might occur between the inner and outer pipe parts is thereby compensated far by a corresponding adjustment in the control valve. External intervention and monitoring are no longer required.

The invention furthermore provides aerodynamically rounded air intakes at the mobile pipe stub. This has not been the case to-date in the previously known testing apparatus and as a result, especially at the high air flows that occur when testing open fabrics, suctionjet contractions occur in the prior art devices, which reduce the effective testing cross-section and thereby introduce results which cannot be compared. This is prevented by the rounded air intake(s). Additionally, the mobile pipe stub has not flow-inhibiting or cross-section varying elements. Also, both pipe stubs and also the air pipe are provided with a polished inner surface. This step minimizes intake and transmission losses and provides an optimum load on the test surface.

The invention moreover provides that the mobile pipe stub is displaceable by means of a pantograph. More advantageously a linear kinematics is provided, which includes substantially linear guide elements consisting of a guide rod and a guide groove enclosing said rod.

In a further feature of the invention, provision is made for a motor generating a defined pressure to move one of the pipe stubs. A motor designed as a doubly acting hydraulic or pneumatic cylinder is especially well suited. The motor permits a continuous setting of the clamping force and furthermore assures that the set clamping force remains constant, whereby the samples always are subjected to the same clamping pressure. Appropriately, an analogue or digital display of the clamping pressure is provided on the mobile double pipe stub. The mobile double pipe stub can be connected by a bell crank to the hydraulic or pneumatic cylinder.

A further design of the invention provides that the pipe stubs can be exchanged as a set. This can be performed, for instance, by screwing them into fitted supports or by using a bayonet lock. In this manner, pipe stubs of different clear cross-sections can be used.

It is further advantageous to insert into all mutually facing end sides of the pipe stubs at least one, and preferably several concentric O-seals of circular or square cross-section. Thereby, a labyrinth effect is obtained, which contributes to preventing the lateral inflow of spurious air, especially at high air flow rates.

In order to uniformly load the test surface and to achieve the best aerodynamic effect, it is furthermore appropriate that the air pipe is coaxial with the inner pipe part of the double pipe stub connected to it and has a length at least twice said air pipe's diameter.

The invention further proposes mounting the volumeter or airflow rate meter in the straight end region of the suction pipe on the exhauster side. This arrangement provides an accurate measurement of the airflow or of the air volume because the long, straight pipe provides as a calming stretch.

Heat-based test instruments have been found to be especially suitable for measuring air flow rates. The hotwire anemometer and even more so a so-called hot-film sensor have been found especially suitable, the latter even more so because it is insensitive to entrained dust particles and impurities. These test instruments are characterized by a very high dynamic range of 1:100 and by very high accuracy. The entire measurement range of the test apparatus therefore can be covered by a single pick-up means. Alternatively, the air flow meter can be designed to be a third differential-pressure meter, in particular jointly with a nozzle or throttle inside the air channel. Obviously, the air flow meter should, in this case too, be connected to an analogue or digital test display.

In a further feature of the invention, the first differential-pressure meter is provided with a pressure tap in each of the two pipe stubs, i.e. at their inner pipe parts. Heretofore, only the vacuum in the exhaust line has been tapped. It is especially advantageous that the pipe stubs or their inner pipe parts comprise several—at least three—pressure taps distributed over the circumference and connected each by means of an annular channel which may be located in the inner pipe part(s), averaging being achieved thereby. For the same reason, the outer pipe part of the immobile double pipe stub should comprise several circumferentially distributed pressure taps.

The invention furthermore proposes hooking up at least one bypass line having a control valve mounted therein to the suction pipe between the air volumeter or air flow rate meter on one hand and the exhauster on the other. If a single bypass line is insufficient to cover the entire range of regulation, it may be advantageous to provide a larger bypass line with a coarse control valve and a smaller bypass line with a fine-control valve. This slitting-up makes it possible, on one hand, to almost completely erase the vacuum generated by the exhauster in order to assure that, even for the case of very dense samples, regulation shall still be operative. On the other hand, following approximate regulation by the coarse control valve in the larger bypass lie, very accurate control will be possible by means of the fine-control valve in the smaller bypass line, with the result being improved testing accuracy. Each of the coarse and fine control valves may be equipped with a setting motor, with the setting motor for the coarse-control valve being connected to a three-position control having an adjustable dead range. The vacuum will be kept constant within this dead range by the fine-control valve. To that end, the differential-pressure pickup and the control valve(s) are mounted in a control loop in order to set and keep constant the differential pressure. In this manner, any changes in pressure are henceforth prevented from affecting the test results as occurred in prior art devices.

The invention further provides that the testing fork, together with all of its parts, is mounted within one housing whereby it can be handled as one unit and acccordingly comprises a caster vehicle so that it can be moved into the sample. Also, a linear guide means can be provided which displaceably supports the test fork and which itself appropriately rests on a vehicle.

In order to measure the central area wide paper-machine felts and dryer fabrics also in the central area, the test fork includes an aperture at least 1.5 m long, with values of about 2 m long desirable.

Lastly, the invention proposes that the blower be in the form of an exhauster generating a vacuum of at least 2 mbars for an open test apparatus. This makes possible a test procedure wherein the test-apparatus loss is eliminated. To that end, the airflow of the open test apparatus at a defined differential pressure is first measured. Then the sample is clamped in place and the air flow is measured at the same differential pressure. The airflow to be assigned to the sample is computed from the difference between the two test values. As a result, values of air permeability can be computed.

The invention is shown in closer detail in the drawing in relation to the diagrammatical illustrative embodiment.

FIG. 2 is a sideview of the inside parts of the test apparatus FIG. 3 is a section along Line A-B of FIG. 2.

Figure 1:
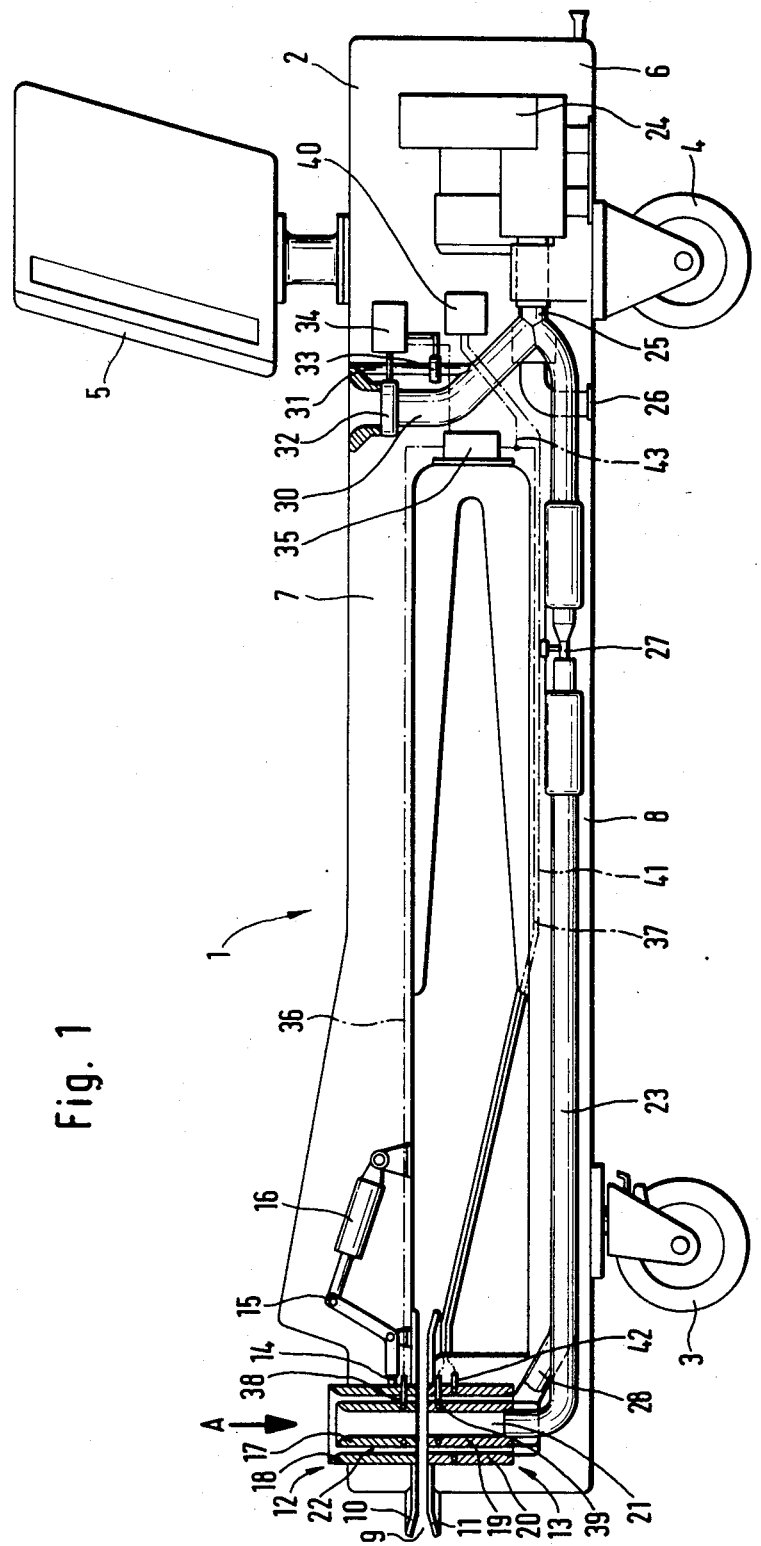
FIG. 1 is a sideview of a test apparatus for paper-machine felts and dryer fabrics

The test apparatus 1 shown at least in part in FIGS. 1 through 3, measures the air-permeability of paper-machine felts and dryer fabrics as well as other substantially incompressable textiles. Essentially, it consists of a test fork 2, of casters 3, 4 mounted thereunder, of a display and operating desk 5 rotatable through 270° and containing the entire electronic of the test apparatus 1. The casters 3, 4 permit the test apparatus to be displaced in any desired direction.

The test fork 2 is provided with hollow self-supporting legs 7, 8 having the same length and projecting from a housing part 6 and furthermore mounted one above the other. At their free ends they provide a clear testing gap 9 bounded by two mutually opposite guide dishes 10, 11. A length of material, for instance papermachine felt, can be inserted between these guide dishes 10, 11, the considerable intake width of the testing fork 2 permitting insertion at a corresponding distance from the edge.

Double pipe stubs 12, 13 are congruently mounted in the legs 7, 8 in coaxial manner with the guide dishes 10, 11. The upper double pipe stub 12 is displaceably guided in the upper leg 7 by a precision linear guide means, not shown herein in further detail, to assume a precise axial direction. This linear guide means consists of three guide rods distributed along the periphery of the double pipe stub 12 and arannged in the axial direction, extending in guide grooves connected to the leg 7. Accordingly the double pipe stub 12 always remains congruent with the lower double pipe stub 13 when in motion.

The upper double pipe stub 12 is linked in articulating manner with an actuating fork 14 rigidly mounted to a bell crank 15. This bell crank 15 is supported in fixed manner in the leg 7 and is connected in hinging manner at the end away from the double pipe stub 12 to a doubly acting pneumatic cylinder 16. This pneumatic cylinder 16 is controlled by a pushbutton actuated electro-valve not shown herein in closer detail. The pressure and hence the clamping force can be set continuously and can then be kept constant. By means of a display, this pressure also is reproducible at any time. Release also is performed through depressing a pushbutton.

Figure 4:
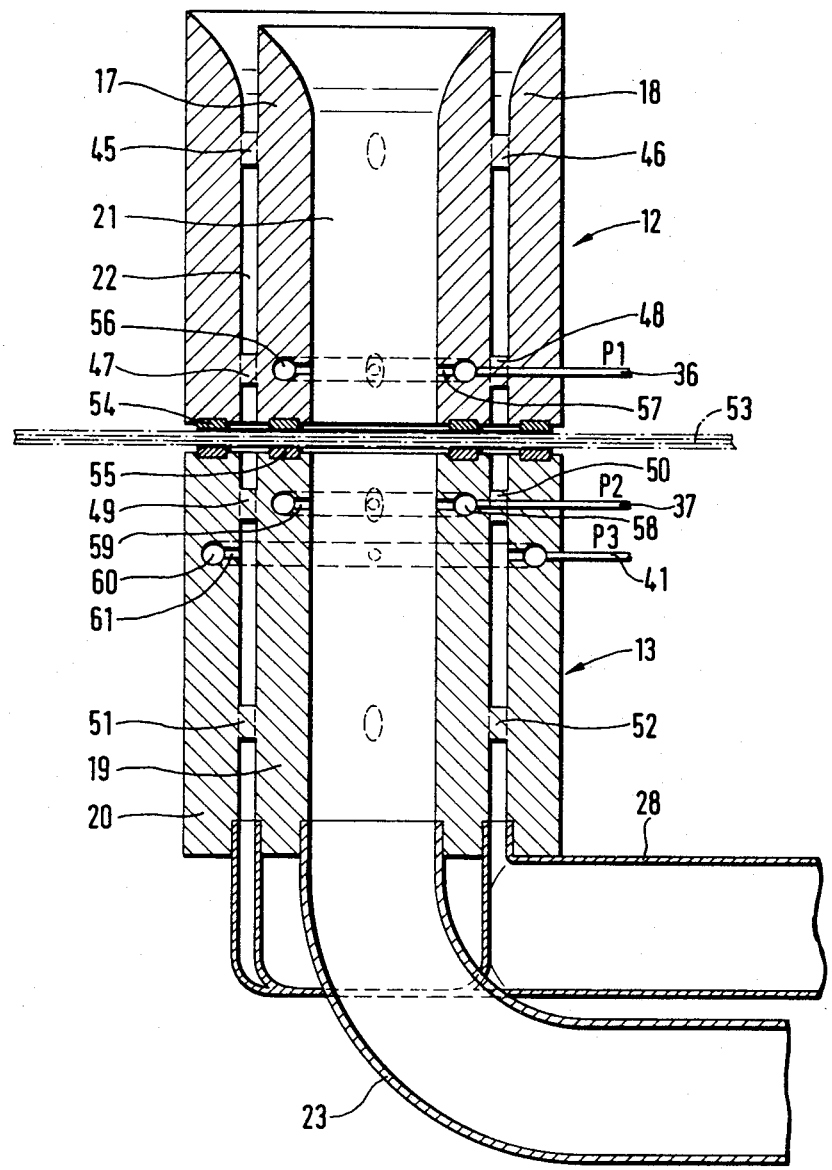
FIG. 4 is an enlarged section of the double pipe stubs of the test apparatus of FIG. 1 through 3.

The upper double pipe stub 12 consists of an inner pipe part 17 and of an outer pipe part 18 coaxially surrounding said part 17 and radially spaced therefrom to provide an annular channel, as best shown in FIGS. 1 and 4. The upper ends of the inner pipe part 17 and the outer pipe part 18 are aerodynamic and therefore no turbulence occurs in this region, and accordingly the test surface is optimally loaded throughout. The arrow A indicates the direction of flow of the air. In addition, the inner and outer pipe parts 17, 18 have the inside surfaces thereof polished.

The lower double pipe stub 13 is mounted in fixed manner to the lower leg 8. Said stub 13 also consists of an inner pipe part 19 and an outer pipe part 20, the inner pipe parts 17, 19 and the outer pipe parts 18, 20 of the two double pipe stubs 12, 13 being congruent in each instance as best shown in FIG. 4. As a result, an inside air channel 21 is obtained which is enclosed by the inner pipe parts 17, 19, together with an external air channel 22 which is annular in crosssection and extends between the outside walls of the inner pipe parts 17, 19 and the inside walls of the outer pipe parts 18, 20.

A suction pipe 23 is connected to the lower end of this inside pipe part 19 and initially extends axially straight and downwards, then after a bend it extends horizontally through the entire leg 8. In this manner, the horizontal section provides a long calming stretch for the pipe flow. The suction pipe 23 issues into an exhauster 24 mounted in a housing part 6. An exhaust air line 25 with a downward exhaust 26, issues from the exhauster 24. An acoustic damper, not shown herein, is additionally installed to reduce flow noises.

A hot-film sensor 27, operating according to thermal measuring principles, is mounted in the region of the suction pipe 23 which is on the exhauster side and thereby provides an air flow meter. Said sensor 27 operates very accurately due to the calmed airflow in this region.

The outside air channel 22 is connected at the lower end of the outer pipe part 20 to a parallel pipe 28 extending, as shown in particular by FIG. 3, parallel to the suction pipe 23 into which it issues shortly ahead of the exhauster 24, and behind the hot-film sensor 27. A control valve 29 is inserted into this parallel pipe 28 to permit the vacuum in the parallel pipe 28 to be set.

A first bypass line 30 is branched at the entry of the parallel pipe 28 into the suction pipe 23. A second bypass line 31 of lesser cross-section issues in turn from the first bypass line 30. The first bypass line 30 includes a coarse control valve 32 and the second one a fine-control valve 33, both valves 32 and 33 being connected to a control means 34. The control means 34 includes regulating electronics and also setting motors for the control valves 32, 33. The control means 34 is coupled to a differential-pressure pickup 35 which is connected by lines 36, 37 to the pressure taps 38, 39 in the inner pipe parts 17, 19 of the double pipe stubs 12, 13.

A regulating device 40 is mounted in the region of the bypass lines 30, 31 and is connected through a line 41 to a pressure tap 42 in the outer pipe part 20. Furthermore the regulating device 40 is connected by a line 43 to the line 37. The regulating device 40 accordingly receives the pressures in the inside air channel 20 and in the outside air channel 22 in the double pipe stub 13. An output line 44 ishooked to the regulating device 40 and leads to a setting motor for the control valve 29.

FIG. 4 is an enlarged representation of the double pipe subs 12, 13 shown in vertical section. The two inner pipe parts 17, 19 are mounted by means of support-ribs 45, 46, 47, 48, 49, 50, 51, 52 to the outer pipe parts 18, 20 in such a manner that a uniform spacing and hence an annular outside air channel 22 is formed. A screen 53 is clamped between the mutually facing ends of the double pipe stubs 12, 13. For that purpose, cross-sectionally rectangular O-rings 54, 55 are received in the end surfaces in order to prevent entry of spurious air. The suction pipe 23 is connected to the inside air channel 21, with the parallel pipe 28 extending from the outside air channel 22.

An annular channel 56 is disposed in the inner pipe part 17 of the upper double pipe stub 12 and is connected by four bores 57, distributed around the periphery, to the inside air channel 21. The line 36 starts from this annular channel 56 and passes through the support ribs 48. Again an annular channel 58 is disposed in the inner pipe part 19 of the lower double pipe stub 13 and forms the beginning of the line 37, being also connected by four bores 59 to the inside air channel 21.

The outer pipe part 20 of the lower double pipe stub 13 is provided with a further annular channel 60 communicating by four bores 61 with the outside air channel 22 and connected to the line 41 to the regulation device 40.

The measurements by means of the shown test apparatus 1 are performed as follows:

After the dryer fabric or fabric strainer 53 is clamped between the double pipe stubs 12, 13 due to the actuation of the pneumatic cylinder 16 exerting a defined pressure, a desired pressure difference, of for instance 2 mbars, is pre-set at the control means 34 when the exhauster 24 is operational. This is followed by the actuation of a three-position control controlling the coarse-control valve 32, the three-position control having a dead range for instance from 1.8 to 2.2 mbars. The coarse control valve 32 then is moved out of the open position until the three-position control senses a pressure difference of 1.8 mbars. Then the fine-control is assumed by the fine-control valve 33 by means of which the pressure-difference is raised to 2.0 mbars and is thereafter kept constant with the highest possibly accuracy.

Simultaneously, the setting motor for the control valve 29 is always so set by the regulation device 40 that the same pressure always is present in the inside air channel 21 and in the connecting suction pipe 23, as well as in the outside air channel 22 and the connecting parallel pipe 28. This procedure prevents spurious air from being sucked through the fabric 53 into the inside air channel 21 and hence into the suction pipe 23. In this respect, the outside air channel 22 assumes the function of blocking the entry of spurious air.

After the setting operation has been completed, the air flow at the hot-film sensor 27 and the reference and measured pressure-differences can be read off the display and operating desk 5 as a measure of the air permeability of the clamped fabric 53. Any changes in pressure-differences in the suction pipe 23 are immediately corrected by the regulation valve 26, with the regulation device 40 assuring that no pressure-difference arises between the inside air channel 21 and the outside air channel 22.

We claim:

1. An air-permeability measuring apparatus for textiles, particularly for paper-machine felts and dryer fabrics, comprising:
    (a) a measuring fork having first and second rigid legs disposed in parallel overlying relation;
    (b) a first double pipe stub displacably mounted to said first leg and said first double pipe stub comprising a first inner pipe stub providing a first inner flow channel and a first outer pipe stub radially spaced from said first inner pipe stub and therewith providing a first annular flow channel;

(c) a second double pipe stub mounted to said second leg and said second double pipe stub comprising a second inner pipe stub providing a second inner flow channel and a second outer pipe stub radially spaced from said second inner pipe stub and therewith providing a second annular flow channel;

(d) said double pipe stubs being coaxial and said first double pipe stub adapted for being displaced between a first insert position and a second clamping position wherein end faces of said double pipe stubs are oppositely disposed for clamping a length of fabric therebetween so that said second inner and annular flow channels commuicate with said first inner and annular flow channels;

(e) pipe means extending from each of said second inner and annular flow channels;

(f) exhauster means operably associated with each of said pipe means for exerting a vacuum on said second inner and annular flow channels and thereby inducing air flow through said first inner and annular flow channels when said first double pipe stub is in said second position;

(g) control valve means operably associated with the pipe means extending from said second annular flow channel for regulating the air flow therethrough;

(h) measuring means associated with the pipe means extending from said second inner flow channel for measuring the air flow therethrough; and, (i) control means operably associated with said control valve means and with said exhauster means for assuring constant pressure on each of said second inner and annular flow channels.

2. The apparatus as defined in claim 1, wherein:
(a) said inner pipe stubs being congruent; and,
(b) said outer pipe stubs being congruent.

3. The apparatus as defined in claim 1, wherein:
(a) said second outer pipe stub having the inside surface thereof spaced from the outer surface of said second inner pipe stub by at least 5 mm.

4. The apparatus as defined in claim 1, wherein:
(a) a plurality of axially spaced rigid ribs extend around each of said inner pipe stubs and are connected to said outer pipe stubs for maintaining uniform spacing of said outer pipe stubs from said inner pipe stubs.

5. The apparatus as defined in claim 1, wherein:
(a) said control means includes a differential pressure meter; and,
(b) a control motor being operatively connected to said control valve means and to said control means for operating said control valve means in response to said control means.

6. The apparatus as defined in claim 1, wherein:
(a) said first inner and outer pipe stubs having aerodynamically rounded air intakes.

7. The apparatus as defined in claim 1, wherein:
(a) said first inner and outer pipe stubs having constant diameter.

8. The apparatus as defined in claim 1, wherein:
(a) said first inner and outer pipe stubs having polished inside surfaces.

9. The apparatus as defined in claim 1, wherein:
(a) a pantograph has a first end portion secured to said first leg and a second end portion secured to said first double pipe stub and is adapted for displacing said first double pipe stub.

10. The apparatus as defined in claim 1, wherein:
(a) linear kinematic means being associated with said first double pipe stub for displacing said first double pipe stub.

11. The apparatus as defined in claim 10, wherein said linear kinematic includes:
(a) guide rod means axially disposed around the periphery of said first double pipe stub; and,
(b) guide groove means enclose said guide rod means.

12. The apparatus as defined in claim 1, wherein:
(a) motor means being operatively associated with said first double pipe stub for generating a defined clamping pressure and for displacing said first double pipe stub.

13. The apparatus as defined in claim 12, wherein said motor means includes:
(a) a double acting cylinder and piston assembly.

14. The apparatus as defined in claim 1, wherein:
(a) display means being associated with said fork for displaying the clamping pressure exerted by said first double pipe stub when in said second position.

15. The apparatus as defined in claim 13, wherein:
(a) a bell crank being connected to said first double pipe stub; and,
(b) said cylinder and piston assembly being operatively connected to said bell crank for displacing said first double pipe stub.

16. The apparatus as defined in claim 1, wherein:
(a) the inner and outer pipe stubs of said first and second double pipe stubs being exchangable.

17. The apparatus as defined in claim 16, wherein:
(a) said double pipe stubs being threadedly received in fitting means associated with each of said legs.

18. The apparatus as defined in claim 16, wherein;
(a) each of said legs having a bayonet fixture; and,
(b) each of said double pipe stubs being held in one of said bayonet fixtures.

19. The apparatus as defined in claim 1, wherein:
(a) seal means being associated with the oppositely disposed end faces of said double pipe stubs.

20. The apparatus as defined in claim 1, wherein:
(a) the pipe means extending from said inner channel has a portion thereof coaxial with said second inner pipe stub and having a length at least twice the diameter of said second inner pipe stub.

21. The apparatus as defined in claim 1, wherein:
(a) the pipe means extending from said second inner pipe stub has a straight section of substantial length upstream of said exhauster means; and,
(b) said measureing means operably associated with said straight section.

22. The apparatus as defined in claim 1, wherein:
(a) said measuring means includes a hot-wire anemometer.

23. The apparatus as defined in claim 1, wherein:
(a) said measuring means includes a hot-film sensor.

24. The apparatus as defined in claim 1, wherein:
(a) said measuring means includes a differential pressure meter.

25. The apparatus as defined in claim 1, wherein:
(a) display means being operably associated with said measuring means for displaying the air flow measured thereby.

26. The apparatus as defined in claim 1, wherein:

(a) each of said inner pipe stubs has at least one pressure tap therethrough communicating with said inner flow channel; and, (b) means operably connect said control means with each of said pressure taps.

27. The apparatus as defined in claim 26, wherein:

(a) at least three pressure taps being circumferentially disposed about each of said inner pipe stubs; and, (b) an annular channel being disposed in each of said inner pipe stubs and communicating with each of the pressure taps of said inner pipe stubs.

28. The apparatus as defined in claim 1, wherein:

(a) a plurality of pressure taps being operably associated with said second outer pipe stub;

(b) an annular channel being disposed in said second outer pipe stub and communicating with each of said plurality of pressure taps; and, (c) means operably connect said annular channel of said second outer pipe stub with said control means.

29. The apparatus as defined in claim 27, wherein:

(a) said means includes test lines having substantially equal length.

30. The apparatus as defined in claim 1, wherein:

(a) said pipe means being interconnected at a point downstream of said measuring means and upstream of said exhauster means so that a pipe portion extends therefrom to said exhauster means; and, (b) a plurality of tests bores being in said pipe portion to permit calibration of said control means.

31. The apparatus as defined in claim 30, wherein:

(a) said pipe portion and said inner and outer pipe stubs of each of said double pipe stubs being electro-chemically polished.

32. The apparatus as defined in claim 30, wherein:

(a) by-pass line means being in flow communication with said pipe portion; and, (b) control valve means operably associated with said by-pass line means and with said control means for regulating flow to said exhauster means.

33. The apparatus as defined in claim 31, wherein:

(a) said by-pass line means includes at least a first and second by-pass line; p1 (b) said first by-pass line having a diameter exceeding the diameter of said second by-pass line; and, p1 (c) each of said by-pass lines having control valve means operably associated therewith whereby said first by-pass line being adapted for generally coarse regulation and said second by-pass line being adapted for accurate fine regulation.

34. The apparatus as defined in claim 33, wherein:

(a) setting motor means associated with each of said control valve means of said by-pass lines for adjusting said control valve means; and, (b) a three-position controller having an adjustable dead range being operably connected to the setting motor of said first by-pass line.

35. The apparatus as defined in claim 33, wherein:

(a) said control means and the control valve means of said by-pass lines being operably interconnected in a control loop adapted for setting and maintaining constant a preselected pressure difference.

36. The apparatus as defined in claim 1, wherein:

(a) said testing fork being mounted in a housing.

37. The apparatus as defined in claim 36, wherein:

(a) a caster system associated with said housing permitting movement of said housing and thereby of said testing fork.

38. The apparatus as defined in claim 1, wherein:

(a) said exhauster means adapted for generating a vacuum of at least 2 mbars when said first double pipe stub is in said first position.

39. An air-permeability measuring apparatus for textiles, particularly for paper-machine felts and dryer fabrics, comprising:

(a) a measuring fork having first and second rigid legs disposed in parallel overlying relation;

(b) pipe stub means displacably mounted to said first leg and providing a first inner flow channel;

(c) a double pipe stub mounted to said second leg and said double pipe stub comprising an inner pipe stub providing a second inner flow channel and an outer pipe stub radially spaced from said inner pipe stub and therewith providing an annular flow channel;

(d) said pipe stub means being coaxial with said inner pipe stub and said pipe stub means adapted for being displaced between a first insert position and a second clamping position wherein end faces of said pipe stub means and said inner pipe stub are oppositely disposed for clamping a length of fabric therebetween so that said inner flow channels communicate;

(e) pipe means extending from each of said second inner and annular flow channels;

(f) exhauster means operably associated with each of said pipe means for exerting a vacuum on said second inner and annular flow channels and thereby inducing air flow through said inner flow channel when said pipe stub means is in said second position;

(g) control valve means operably associated with the pipe means extending from said second annular flow channel for regulating the air flow therethrough;

(h) measuring means associated with the pipe means extending from said second inner flow channel for measuring the air flow therethrough; and, (i) control means operably associated with said control valve means and with said exhauster means for assuring constant pressure on each of said second inner and annular flow channels.

40. The apparatus as defined in claim 39, wherein:

(a) said pipe stub means includes a double pipe stub comprising an inner pipe stub providing said first inner flow channel and an outer pipe stub radially spaced from said inner pipe stub of said pipe stub means and providing therewith an annular channel; and, (b) said inner and outer pipe stubs of each of said double pipe stubs being congruent.

* * * * *